United States Patent [19]

Vulic

[11] Patent Number: 4,573,655
[45] Date of Patent: Mar. 4, 1986

[54] SWIVEL CLAMP

[76] Inventor: Sekula Vulic, 319 E. 17th Ave., Columbus, Ohio 43201

[21] Appl. No.: 669,595

[22] Filed: Nov. 8, 1984

[51] Int. Cl.⁴ ............................................. A47G 29/00
[52] U.S. Cl. .................................... 248/278; 248/124; 403/53; 403/146
[58] Field of Search ................. 248/70, 124, 276, 278, 248/289.1, 291; 403/146, 94, 96, 93, 92, 72, 53, 57

[56] References Cited

U.S. PATENT DOCUMENTS

| | | | |
|---|---|---|---|
| 802,705 | 10/1905 | Parker | 248/291 |
| 951,324 | 3/1910 | Mayer | 403/93 |
| 1,439,914 | 12/1922 | Saxe | 403/96 |
| 1,509,381 | 9/1924 | Townsend | 403/57 |
| 2,241,506 | 5/1941 | Eppler | 403/146 |
| 2,432,098 | 12/1947 | Horn | 403/57 |
| 2,551,136 | 5/1951 | Keltner | 403/53 |
| 2,553,158 | 5/1951 | Zillman | 403/146 |
| 2,886,998 | 5/1959 | Scott | 403/92 |
| 4,392,323 | 7/1983 | Rubik | 403/96 |

Primary Examiner—J. Franklin Foss
Assistant Examiner—Robert A. Olson
Attorney, Agent, or Firm—Frank H. Foster

[57] ABSTRACT

A multiple jointed support member comprising three members normally aligned in a generally co-planar end to end relationship. One of the members disposed at one end of the support has a swivel joint connection to the centrally disposed member. The other member disposed at the opposing end is provided with a hinged joint connection to the centrally disposed member and has an axis of rotation disposed at right angles to the axis of rotation of the swivel joint connection. Spring members are associated with each of the joint connections to bias each of said outer elements toward the central element in multiple, releasably latched positions about the axis of rotation of the respective pivot pins associated with each of said joint connections.

11 Claims, 8 Drawing Figures

1

SWIVEL CLAMP

BACKGROUND

The field of joint connections is very old and such prior art exists. However, the prior art has not provided a simple and yet reliable multiple joint support member which interconnects three members to one another with two joints having their axis of rotation disposed at right angles to one another and include means to bias said elements together in a normal co-planar position as well as preselected releasably latched positions rotated from said normal position.

One application for such a multi-jointed support member relates to a support clamp which may be used to mount an intervenous multiple transducer plate or holder to a conventional pole support for use with delivering intervenous solutions to patients such as commonly used in hospitals. In such an application, it is required to "prime" the conduit tubing communicating the solution to the transducers by removing any entrapped air prior to operating the valves to feed the solution to the patients.

Prior to the present invention there were no clamp support means to provide a convenient or facile means to accomplish this maneuver which requires the transducer plate or holder to be rotated or turned upside down and then returned to the right side up position while the whole assembly was connected to and supported upon the I.V. pole support.

Therefore, routinely this priming action was accomplished by manually rotating the transducer holder and any associated valve means using both hands after the assembly was removed from the I.V. pole. During emergency situations, since there is no other support holding the assembly, inadvertent dropping of the whole assembly during this required manuveur has caused serious delay in administering the needed fluids. Additionally this maneuver requires the use of both hands, thus preventing the nursing personnel from having one hand free to assist other personnel or perform other duties.

In this application, it is also desirable to be able to position the transducer holder in various positions relative to a normally co-planar position with the remaining support structure. The hinge-like joint connection makes this possible to provide easy multiple positioning of any device mounted thereto by rotating this member about an axis disposed at ninety degrees to the axis of the other joint connection.

SUMMARY OF INVENTION

The present invention relates to a multiple jointed support member having novel joint interconnection means between the members which have their axis of rotation disposed at right angles to one another. Each of the joint interconnections are provided with novel features including biasing the elements of the support member in multiple releasably latched positions.

One of said novel joint connections includes a connecting pivot pin which is mounted longitudinally through two elements of the support to connect them in an end to end relationship. A spring means is mounted along the length of the pin in a manner to bias the elements toward one another in said end to end relationship. A thrust bearing is mounted on one end of the pin and forms one seat for the spring to prevent undesirable rotation of a threaded fastener on the pin which serves to facilitate fabrication and to adjust the biasing force on the spring. A tongue and groove or appropriate recesses may be provided to releasably fix the members in a given position of rotation about the pin.

The other novel joint connection features a flexible shaft element or pin which is mounted through hinge-like portions formed on two of the elements forming the support. The resilient pin is disposed parallel to adjoining end portions of the elements connected thereto. These end portions are provided with elevated portions to vary the radius of the pivoting movement against the biasing force of resilient pin to permit relative rotation of the elements about the axis of the resilient pin in multiple releasably latched positions.

The dual jointed support member can be provided with various modifications to serve in a variety of applications to support other elements attached thereto in multiple positions as may be desired.

OBJECTS

It is a primary object of the present invention to provide a unique three element support member provided with novel multiple joints capable of rotation at right angles to one another between preselected releasably latched positions.

It is another object to provide such a support member wherein each of the joint connections are uniquely constructed to permit relatively simple and inexpensive manufacture of a highly versatile multi-position support device.

It is another object of the present invention to provide a device of the type described which is easy to operate to change the relative disposition of either of the jointed members relative to the centrally disposed member or to one another.

It is still a further object of the present invention to provide a device of the type described which possesses the versatility to be adapted to many applications, such as a clamp support or the like wherein at least two different rotational axis are desirable for separate elements of the support.

IN THE DRAWINGS

DETAILED DESCRIPTION

Figure 1:
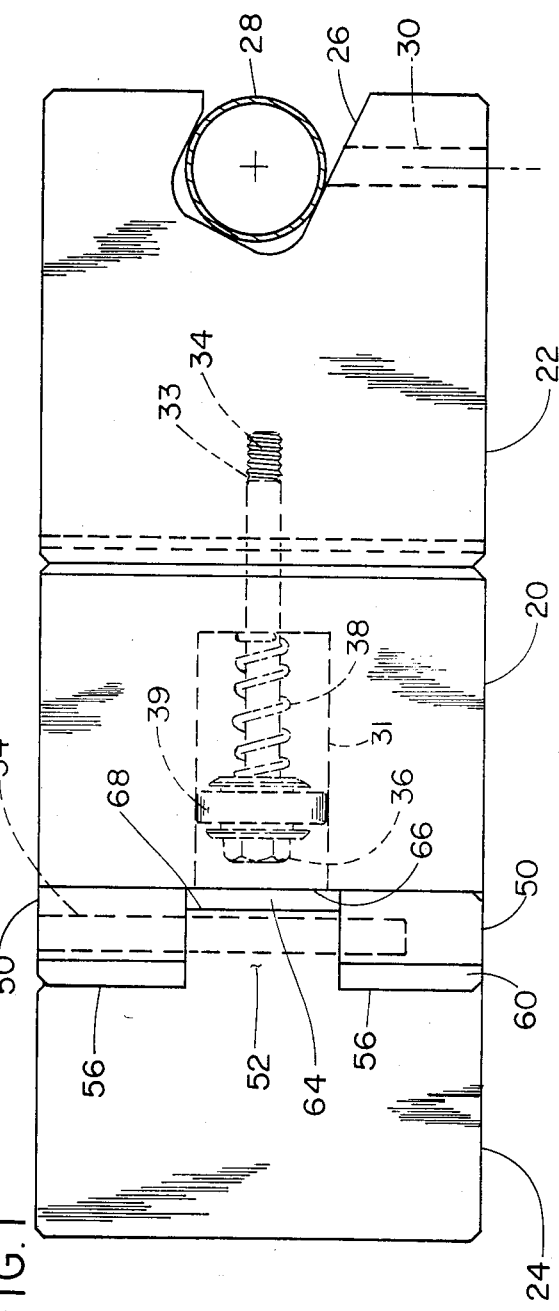
FIG. 1 is a top plan view of a multi-jointed support clamp device constructed in accordance with the present invention.
Figure 2:
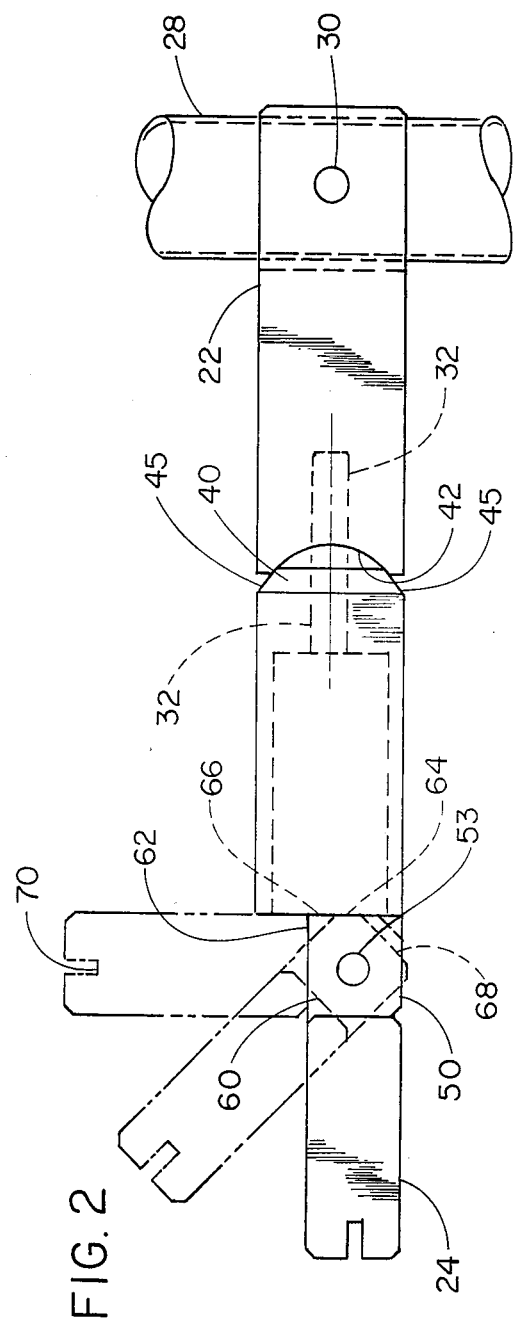
FIG. 2 is a side elevational view of the clamp member shown in FIG. 1 which illustrates in ghost lines one of the end members rotated to other releasably fixed positions.
Figure 2A:
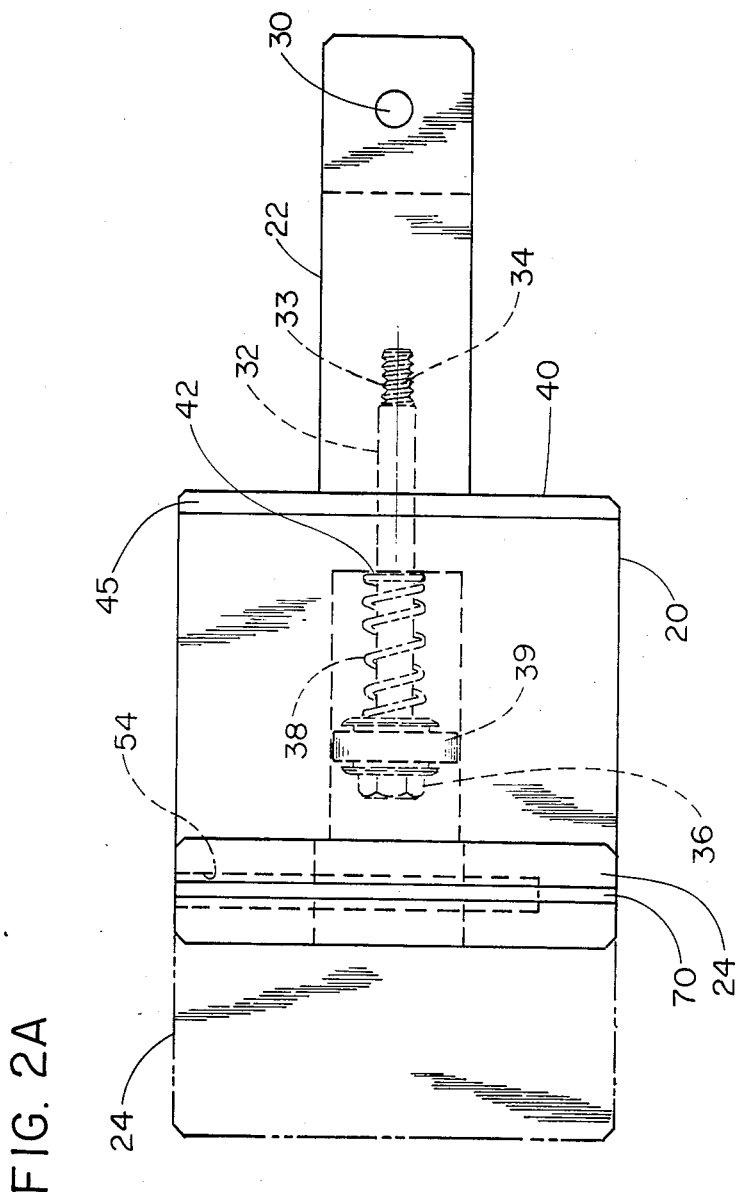
FIG. 2A is a side view of the device as shown in FIG. 3 wherein the rotated end member shown in FIG. 2 and the central member are rotated to another position relative to the right end member as shown in FIG. 2.

A multi-jointed support clamp constructed in accordance with the present invention is illustrated in FIGS. 1 and 2 and includes right and left end members 22 and 24 disposed in a normally generally co-planar end to end relationship with a central member 20. Merely for purposes of illustration, end member 22 is shown fixed to a pole support, such as an I.V. pole used in hospitals. However, the invention is not limited to such an application nor the manner of fixing any one of said members to another body to utilize the advantages of the present invention.

As shown in FIGS. 1 and 2, member 22 is provided with an appropriate recess 26 adapted to receive a pole support 28. A threaded hole 30 is provided to receive a threaded bolt, not shown, for purposes of releasably fixing member 22 to pole 28.

Members 20 and 22 are joined in abutting end to end relationship by means of a pin 32 disposed longitudinally through an internal passage provided in said members.

As viewed in FIG. 1, one end of pin 32 includes a threaded portion 34 fixed in position within, a threaded bore 33 provided in member 22. The opposing end of pin 32 is provided with a threaded end adapted to receive a threaded nut member 36. A compression spring 38 is mounted in surrounding relationship to a portion of pin 32 between a seat portion provided within an internal passage or bore 31 extending into member 22 and a thrust bearing 39 interposed around pin 32 between the end of spring 38 and nut member 36. In this manner members 20 and 22 are connected and biased towards one another by the force of spring 38. However, members 20 and 22 are free to rotate relative to one another about the axis of pin 32.

Thrust bearing 39 prevents undesirable rotational forces to be applied to the threaded cap 36 when members 20 and 22 are rotated relative to one another.

Figure 3:
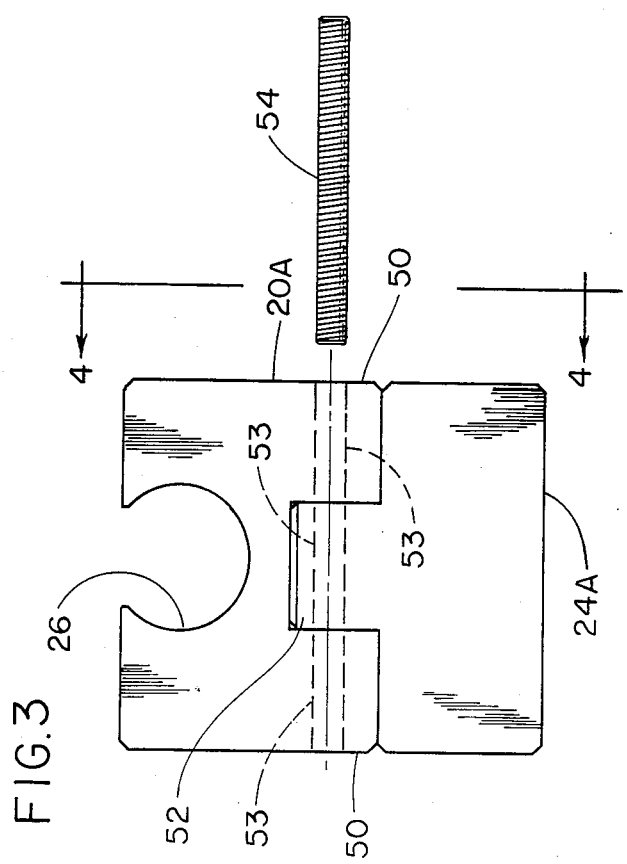
FIG. 3 is a top plan view of the joint connection for two members rotatably joined in the same manner as the left end and central members of the embodiment shown in FIG. 1 with the resilient pin joining the members shown removed from the members.

As best seen in FIG. 2, the right end of member 20 is provided with a reduced end portion forming a tongue 40 which is adapted to be received in a groove or recess 42 extending along the end portion of member 22 facing member 20. When tongue 40 is disposed in groove 42, members 20 and 22 are effectively latched in this position. They may be unlatched to allow relative rotation only upon ovecoming the biasing force of spring 38. Therefore as shown in FIGS. 1 and 3, it should be understood that when member 22 is fixed, such as to pole 28, member 20 can be rotated around the axis of pin 32 and releasably locked into a given position when tongue 40 again mates within groove 42. Other releasably locked angular positions may be obtained by providing recesses intersecting groove 40 such as illustrated in the embodiment shown in FIG. 6.

It should be noted that the angular outer edge portions 45 of tongue 40 and the radius of groove 42 tend to reduce the effort of overcoming the biasing force of spring 38 to aid one to release the members from the latched position when rotation is required.

Still referring to FIGS. 1 and 2, a second joint connection is shown involving members 20 and 24 wherein the left end of member 20 includes a pair of ears or outwardly extending hinge members 50. Member 24 includes an ear or hinge member 52 adapted to be received between hinge members 50. Each of the hinge members 50 and 52 are provided with a through-hole, such as 53, which forms a receiving passage for a resilient pin member 54 when the hinge members 52 and 50 are properly disposed to align the through-holes 53 with one another. Preferably, pin member 54 fits within the aligned holes 53 in a slightly snug relationship.

The left end portion of member 20 and outer end portions of hinge members 50 include generally flat surface portions which face one another in engaging relationship along line 56, as viewed in FIG. 1, when the members are disposed in the normal co-planar relationship in which the holes 53 of hinge members 50 and 52 are in aligned relationship. However, the outer facing surface of hinge portions 50 include at least one beveled corner forming a surface 60 inclined relative to the engaging flat surfaces meeting along line 56. This permits member 22 to be rotated about the axis of pin 54 to the positions as shown in ghost lines in FIG. 2. As viewed from the side, the corners of the beveled surface portion form raised points relative to a normal radius of rotation of member 24 about the axis of pin member 54 which is related to a radius measured between the axis of pin 54 and the engaging flat surfaces defining line 56.

Therefore, in order for element 24 to be rotated, pin member 54 must be bent out of its normal straight alignment to allow for the lengthened radius of the rotational movement between the members. During this rotation, hinge portion 52 is slightly displaced out of the original alignment such that the through-hole 53 in hinge member 52 is not aligned with the through-holes 53 in hinge members 50 of member 20.

The stiffness of the pin member 54, preferably in the form of a compression spring, determines the force necessary to apply to distort pin member 54 in order to permit movement of member 24 relative to member 20.

When the flat surface portion of member 24 is parallel with the beveled surface 60, the through-holes 53 in hinge members 24 are re-aligned and the pin member 54 returns to its original normally straight condition. This provides a latched or relatively stable condition to the new position of members 20 and 24.

A third latched position is provided when member 24 is forced over the other corner of beveled surface 60 until the flat inner surface of member 24 is parallel to the flat surface of indented or recessed surface 62 provided on the upper surface of member 20. The relationship described above between the through-holes 53 and pin member 54 occurs again during this rotational movement of member 24. Of course it is repeated when member 24 is returned to either of the previously described positions.

To compliment the releasably locked or latched positions described, a beveled surface 64 is provided on the innermost surface of hinge member 52 which functions in a similar manner as described in relationship to surface 60. However, beveled surface 64 is inclined in the opposite direction compared to surface 60 and cooperates with the outer flat surface 66 of member 20 and a flat surface portion 68 of hinge member 52 to compliment the rotation of the members 20 and 24 to the releasably locked positions described above.

For purposes of example only, a slot 70 is shown in FIG. 2 which extends the width of the outer end of member 24. Such a slot may be provided to removably receive a thin plate, for example, upon which a plurality of valves and/or transducer elements are mounted such as used in connection with intervenous feeding of hospital patients. However, other objects or other connecting or mounting means can be employed for this or other applications without departing from the spirit of the present invention.

Figure 4:
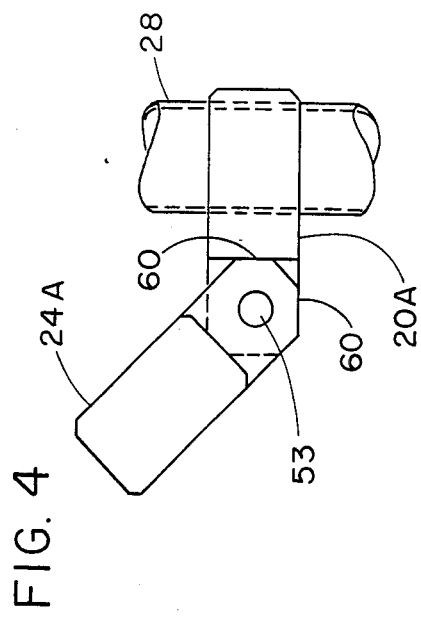
FIG. 4 is a side elevational view of the embodiment shown in FIG. 3 illustrating the members rotated forty-five degrees relative to another.
Figure 5:
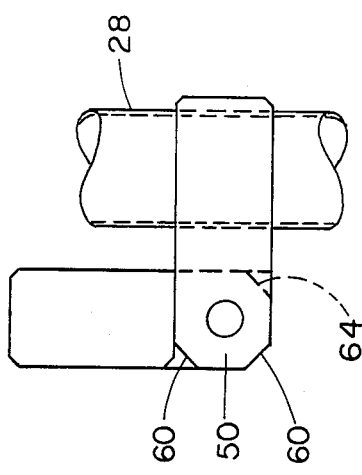
FIG. 5 is a similar view to that shown in FIG. 4 illustrating another position of the members rotated ninety degrees relative to one another.

Referring to FIGS. 3,4 and 5, the movable joint connection described in relation to members 20 and 24 is shown in another embodiment wherein only one joint connection is required involving two members 20A and 24A. The same reference numerals are used in describing this embodiment for those elements which are essentially identical to the embodiment shown in FIGS. 1 and 2.

As best seen in FIGS. 3, 4 and 5, member 20A is provided with an arcuate recess 26 to permit mounting it on a pole support 28 and includes hinge members 50. Members 24A is provided with a hinge member 52 which is adapted to fit between members 50 such that the hole or passage 53 in each hinge member is aligned to receive resilient pin members or spring 54.

As previously described, member 24A may be rotated about the axis of pin 54 to the forty-five and ninety degree positions shown in FIGS. 4 and 5.

The only functional difference between embodiment shown in FIGS. 3-5 is that two beveled surfaces 60 are provided on the opposing ends to also permit members 24A to be rotated to a forty-five and ninety degree latched position in the opposite direction as shown in FIGS. 4 and 5. Therefore, element 24A is provided with five different latch positions relative to member 20A.

In a similar manner, the complimentary beveled corner surfaces 64 are provided on the inner facing surface portion of hinge portion 52 to operate in a similar manner as previously described herein.

Figure 6:
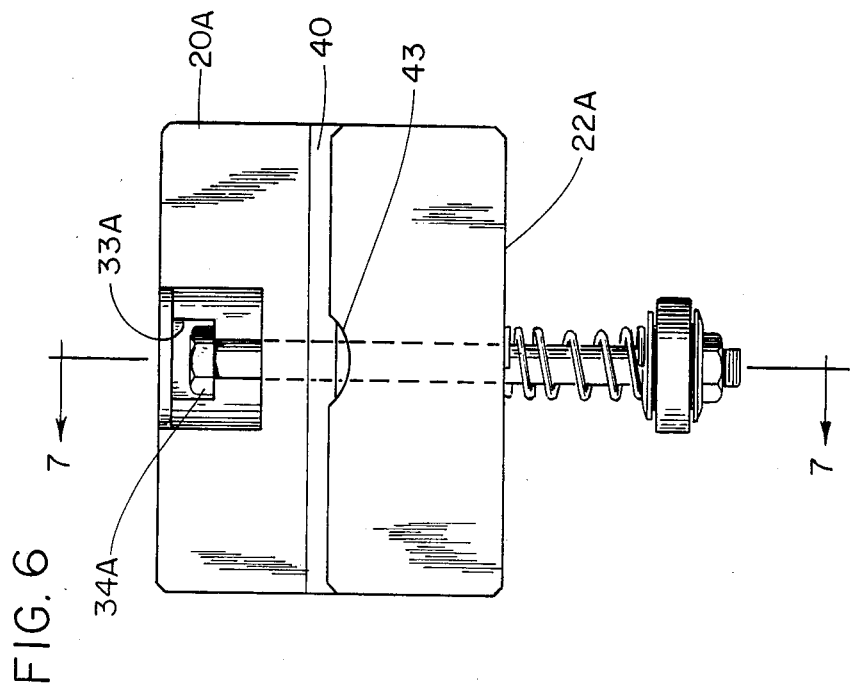
FIG. 6 is another embodiment of the present invention illustrating a joint connection between two members identical to the connection between the right end and central members of the embodiment shown in FIG. 1.
Figure 7:
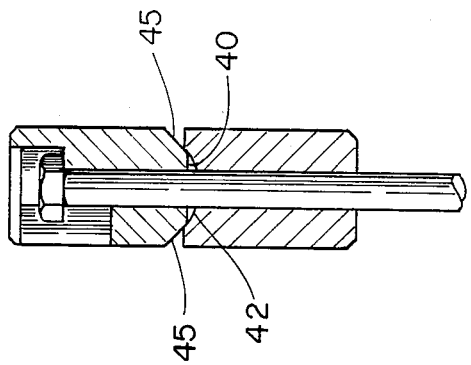
FIG. 7 is a partial side elevational view of the embodiment shown in FIG. 6.

Referring now to the embodiment shown in FIGS. 6 and 7, a two member device is shown which incorporates the pivot connection essentially the same in function as described in the embodiment of FIGS. 1 and 2 relative to members 20 and 22. Members 20A and 22A are interconnected to rotate relative to one another about pin or shaft 32. One end of pin 32 is fixed in any suitable manner to member 20A, such as by means of an enlarged head portion 34A which is adapted to be received in an appropriate recess 33A. The other end of pin 32, shown extending entirely through member 22A, includes the identical spring 38, thrust bearing 39, and cap screw 36 as previously described herein.

A tongue 40 on members 20A extending along one end thereof is adapted to fit within groove 42 in the adjoining end of members 22A to releasably latch the members in their normal end to end relationship.

The embodiment of FIGS. 6 and 7 also illustrate a recess 43 intersecting groove 42 at substantially a right angle to provide additional releasably latched positions between the members 20A and 22A when tongue 40 rotated to be received within the recess 43. Similar to the tongue and groove construction previously described in FIGS. 1 and 2, preferably tongue portion 40 is provided with angled outer portions 45 which tend to ease the effort required to overcome the bias force of spring 38 to remove tongue 40 from groove 42 or recess 43.

Therefore, it should be readily apparent from the foregoing description that a unique multi-joint support member is provided which incorporates novel joint connections to provide a very versatile device for many useful applications. One such joint connection permitting pivotal type multi-positioning and the other serving in the nature of a multiple position hinge-like device.

What is claimed is:

1. A support member having compound joints comprising, in combination, at least three generally flat members normally disposed in abutting, generally parallel end to end relationship, a first one of the outermost end members being connected at one edge to the centrally disposed member for rotational movement about an axis extending parallel to the normal disposition of said members and having means at its opposite edge for attachment to an I.V. pole said first member and said central member having engaging means for retaining them at a plurality of releasably fixed positions; and the second, oppositely disposed end member being movably connected at one of its edges to said centrally disposed member for movement about an axis disposed substantially at a right angle to the rotational axis of said other first outermost end member said second member and said central member having engaging means for retaining them at a plurality of releasably fixed positions, wherein said support member permits single-handed rotation of said transducers for priming.

2. The device defined in claim 1 wherein said first member is rotatably mounted to a pin member fixedly disposed to one of said central member or said first outer member and extending into the other member in a co-planar relationship with said members; and spring means mounted about said pin member to bias said central member and said outer member toward one another.

3. The device defined in claim 2 wherein one end of said pin member includes a threaded portion for receiving a threaded female member and a thrust bearing member forming a spring seat between the end of said spring means and said threaded female member, linear movement of said female member along said threaded portion of pin member serving to vary the tension of said spring means.

4. The device defined in claim 3 wherein the adjacent end portions of said first outermost member and said central member carrying said threaded pin member are provided with a tongue and groove which mate with one another when said members are disposed in said normal parallel end to end relationship to one another.

5. The device defined in claim 4 wherein said member provided with said groove includes at least one recess intersecting said groove at a predetermined angle and is adapted to receive a portion of said tongue to form a second releasably latched position between said members.

6. The device defined in claim 1 wherein the inner end of said second outermost member and the abutting end of said centrally disposed member include aligned hinge means; a resilient shaft means is disposed through said aligned hinge means to connect said members to one another for rotational movement about the axis of said shaft means, at least one of said aligned hinge means includes a surface extending generally parallel to the axis of said shaft and engages an opposing surface of the other of said hinge means, at least one of said engaging surfaces being provided with elevated portions which vary the radius of rotation relative to the axis of said resilient shaft means during relative rotation of members about the axis of said flexible shaft for releasably locking said hinge means in multiple positions relative to one another.

7. The device defined in claim 6 wherein said resilient shaft comprises a coiled compression spring.

8. The device defined in claim 6 wherein generally flat surface portions inclined relative to one another and extending parallel to the axis of said shaft extend between said elevated portions wherein relative rotational movement between said engaging surfaces increases the radius of rotation of said members about the normal axis of said resilient shaft means to cause said shaft means to flex against the normal bias force tending to return said shaft means to a normal unflexed position.

9. A support member comprising in combination, two generally flat members normally disposed in generally co-planar end to end abutting relationship; a pin mounted within said members with its longitudinal axis extending at right angles to the ends of said members abutting one another, one end of said pin being fixed to one of said members and the opposing end of said pin including a removable retaining means; a spring means mounted about the axis of said pin and abutting against a seat provided on one of said members and a thrust bearing disposed between the opposite end of said spring and said retaining means; wherein the entire abutting end of one of said members is formed with a groove extending therealong and the entire abutting end of the other member is formed with a tongue extending therealong adapted to mate with the groove; wherein each of said members may be rotated relative to the other of said members about the axis of said pin.

10. A support member comprising, in combination, at least two members disposable in generally co-planar end to end abutting relationship, the abutting ends of said members including aligned hinge means having a bore receiving a resilient shaft means connecting said members to one another with the longitudinal axis extending generally parallel to the abutting ends of said members; each of said hinge means being provided with engaging surfaces at least one of said engaging surfaces being provided with elevated portions which vary the radius of rotation relative to the axis of said flexible shaft means during relative rotation of said members for releasably locking said hinge members in multiple positions relative to one another between the elevated portions.

11. The device defined in claim 10 wherein generally flat surface portions extend between said elevated portions inclined relative to one another and extending parallel to the axis of said shaft means wherein relative rotational movement between said engaging surfaces increases the radius of rotation of said members about the normal axis of said shaft means to cause said shaft means to flex against the normal bias force tending to return said shaft means to a normal unflexed position.

* * * * *